(12) United States Patent
Bellos et al.

(10) Patent No.: US 7,588,734 B2
(45) Date of Patent: Sep. 15, 2009

(54) LABORATORY REACTOR FOR STUDYING GASEOUS AND LIQUID PHASE REACTIONS

(75) Inventors: Georgios Bellos, Zografos Athens (GR); Pierre Galtier, Vienne (FR); Nikolaos Papayannakos, Vironas Athens (GR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 84 days.

(21) Appl. No.: 11/405,677

(22) Filed: Apr. 18, 2006

(65) Prior Publication Data

US 2007/0071664 A1 Mar. 29, 2007

(30) Foreign Application Priority Data

Apr. 18, 2005 (FR) .................................. 05 03921

(51) Int. Cl.
*B01J 19/00* (2006.01)
*B01J 8/02* (2006.01)
*B01J 35/02* (2006.01)
*G01N 31/10* (2006.01)

(52) U.S. Cl. ................. 422/130; 422/129; 422/211; 436/37

(58) Field of Classification Search .............. 422/130, 422/211, 129; 208/208 R; 261/75; 436/37
See application file for complete search history.

(56) References Cited

U.S. PATENT DOCUMENTS

| | | | | |
|---|---|---|---|---|
| 3,095,274 A * | 6/1963 | Crawford | ................. | 423/649 |
| 3,578,405 A * | 5/1971 | Woodle | ................. | 436/140 |
| 3,933,991 A * | 1/1976 | Dorn et al. | ................. | 423/535 |
| 5,266,270 A | 11/1993 | Ajot et al. | | |
| 5,939,032 A * | 8/1999 | Kang et al. | ................. | 422/211 |
| 6,737,026 B1 | 5/2004 | Bergh et al. | | |

FOREIGN PATENT DOCUMENTS

| EP | 538678 A2 * | 10/1992 |
|---|---|---|
| SU | 1 333 402 A | 8/1987 |
| SU | 1333402 A1 * | 8/1987 |

OTHER PUBLICATIONS

Englisk Translation of Abstract of SU 1333402 A1.*
English Translation of SU 1333402.*
Temkin et al, Laboratory Reactor with Ideal Displacement, 1969, Physicochemical Institute, Moscow, Translated from Kinetika i Kataliz, vol. 10, No. 2, pp. 461-463.*
Hagadus et al, An Improved Single-Pellet Reactor to Study the Interaction of Kinetics with Mass Transfer Effects in Heterogeneous Catalysis, 1972, Industrial & Engineering Chemistry Fundamentals, vol. 11, No. 4, pp. 579-584.*
Database WPI Week 198815; Derwent Publications Ltd., London, GB; AN 1988-103670; XP002362366.

* cited by examiner

*Primary Examiner*—Walter D Griffin
*Assistant Examiner*—Natasha Young
(74) *Attorney, Agent, or Firm*—Millen, White, Zelano & Branigan, P.C.

(57) ABSTRACT

The invention describes a laboratory reactor for the kinetic study of catalytic reactions calling for a gaseous reaction phase and a liquid reaction phase, characterized by a capillary shape, a substantially uniform arrangement of the catalyst grains along the reactor, with, on average, every cross-section of the reactor comprising a defined and constant number of catalyst grains, and this number of grains being between 1 and 4. The reactor that is the object of the invention is especially well suited for studying reactions of hydrogenation, hydrotreatment, and hydrocracking.

21 Claims, 2 Drawing Sheets

LABORATORY REACTOR FOR STUDYING GASEOUS AND LIQUID PHASE REACTIONS

FIELD OF THE INVENTION

The field of the invention is that of laboratory reactors that make it possible to obtain information on the kinetics of reactions that are then used to simulate an industrial reactor. These laboratory reactors are generally of small size with treatment capacities of roughly a few tens of cubic centimeters per hour. They are generally fixed-bed tubular reactors, often operating in the isothermal mode.

The problem posed by this type of reactors, more especially when they are used to study high-speed chemical reactions, is that of limitations on the transfer of material between the gaseous phase and the liquid phase. This problem is generally solved by filling the interstitial volume of the catalytic bed with inert particles of very small grain size or by transforming the flow of fluids from the descending into the ascending mode. The interstitial volume of the bed is defined as the volume of space between the grains comprising said catalytic bed.

This effect of dilution of the catalytic bed or of modification of the flow, however, is not always sufficient to eliminate the hydrodynamic resistance external to the grain, generally called extra-granular resistance by one skilled in the art.

The object of this invention is to describe a new type of laboratory reactor in which the effects of limitation of mass transfer are eliminated without having to modify the grain size or to dilute the catalytic bed.

Finally, the reactor according to the invention allows access to the intrinsic kinetics of the catalyst, i.e., to the kinetics under conditions in which the extragranular resistance is eliminated.

Examination of Some Prior Laboratory Reactors

By far most laboratory reactors described in the literature are fixed-bed tubular reactors, generally in gas and liquid co-current, and in which an attempt is made to keep the liquid volumetric flow rate at a value near the value of the future industrial reactor.

The volumetric flow rate of a gaseous or liquid phase is defined as the ratio of the flow rate of the phase under consideration to the volume of the catalyst expressed in homogenous units.

The superficial velocity of a gaseous or liquid phase is defined as the ratio of the volumetric flow rate of the phase under consideration to the geometrical cross-section of the reactor.

Given the ratio of heights between the laboratory reactor and the industrial reactor that can easily reach $1/100$ or less, it is generally not possible to maintain the superficial velocity of the phase under consideration at the same time.

Laboratory reactors are generally used to perform tests of catalysts and are known under the name "microreactors." are fixed-bed reactors operating under isothermal conditions, with ratios of height to diameter of generally between 15 and 30. The superficial velocities of the reaction phases are much less than in the industrial reactor, typically roughly 100 times less, which can lead to a certain number of undesirable effects, such as defective wetting of the grain, and possible failures of the flow of the phase under consideration within the catalytic bed.

A good description of these laboratory reactors can be found in the work of P. Trambouze, H. Van Landeghem and J. P. Wauquier, "Chemical Reactors," published in the Technip Editions.

To overcome this problem, a first approach is to reduce the size of the particles of said catalyst, which leads to working with a crushed catalyst. This effect of reduction of the grain size, however, changes the kinetic conditions and the selectivity of the catalyst, such that the results are difficult to use to simulate the industrial reactor.

Another approach generally used to overcome this problem is that of introducing a population of fine, inert particles into the interstitial space in order to increase the external wetting of the catalyst, but this approach is not completely reproducible and for this reason entails uncertainty in the kinetic results obtained.

Another approach consists in feeding fluids entering the reactor in the ascending mode in order to completely wet the grains. The application of this method is very often limited due to the occurrence of a backmixing phenomenon in the liquid phase.

The originality of the reactor according to the invention relative to the laboratory reactors of the prior art is precisely to maintain at the same time the volumetric flow rate such as is provided on the future industrial reactor, and the superficial velocities of the reaction phases that dictate the flow mode of said phases around the grain.

This maintenance of the characteristics of the catalyst grain and of the flow around this grain makes it possible to achieve the industrial reactor kinetics with a minimum of bias (or artefacts) linked to the hydrodynamics and to the limitations due to extra-granular mass transfer.

In the prior art, another family of reactors that is called monolithic reactors can be cited; they are formed by a plurality of parallel channels cut into a piece of cordierite, or an equivalent material. This type of reactor can typically be found in catalytic converters for automobiles. In contrast to the laboratory reactor that is the object of this invention, however, a monolithic-type reactor generally implements a single-phase gas reaction, and the catalyst can be found deposited on the wall of the channels, whereas in our case the catalyst is composed of grains that occupy the reactor section in a uniform manner as will be explained in detail below.

SUMMARY DESCRIPTION OF THE FIGURES

SUMMARY DESCRIPTION OF THE INVENTION

Figure 1:
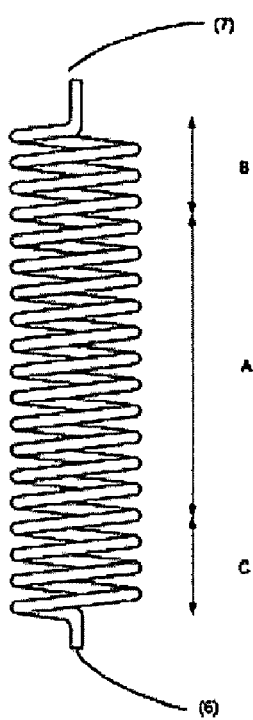
FIG. 1 is a general outline of the reactor according to the invention in a spiral shape.

The invention consists of a laboratory reactor of the tubular type characterized by a substantially uniform arrangement of the catalyst grains within said reactor and by a well-defined ratio between the characteristic dimension of the grains and the tube diameter.

To the degree in which the length of this reactor is much greater than its diameter, at least on the order of 100 times greater, this reactor will be called a "capillary reactor" in the rest of the text below to distinguish it from the reactors according to the prior art that also often have a tubular shape, but with a length/diameter ratio that is much smaller than that of the reactor that is the object of this invention.

The reactor diameter is determined such that only a well-defined and constant number of grains can be installed on average in every section of the reactor, for example 1, 2, 3 or 4 grains. The grains are thus arranged in an ordered manner, and on average in every cross-section of the reactor, and the geometry formed in this way, especially the distance separating the grains from the reactor wall, is then well defined and reproducible.

Of course, depending on the flow rate of the feedstock to be treated, it is possible, if necessary, to arrange in parallel several identical capillary reactors gathered under a single external envelope. This configuration of several parallel and identical capillary reactors remains completely within the framework of the invention, but for ease of understanding, the description that follows will apply to a single reactor.

The reactor according to the invention can thus be defined as a laboratory reactor for the kinetic study of catalytic reactions calling for a gaseous reaction phase and a liquid reaction phase, characterized by a capillary shape, a uniform arrangement of the catalyst grains along the reactor, every cross-section of the reactor comprising a defined and constant number of catalyst grains, and this number of grains being between 1 and 4.

The laboratory reactor according to the invention will have a diameter such that the ratio of the diameter of the reactor to the equivalent diameter of a catalyst grain is constant over the entire length of the reactor and depends solely on the number N of grains contained in every cross-section of the reactor. In the particular case in which the grain number per reactor section is 1, the ratio between the diameter of the reactor and the equivalent diameter of the grain is less than 2, and preferably between 1.1 and 2.

The total catalyst mass that is introduced is generally between 0.1 and 50 grams, and preferably between 1 and 10 grams.

The superficial velocity of the liquid phase is generally greater than 0.3 mm/s, and preferably greater than 0.5 mm/s.

The tube or tubes comprising a reactor module can be rolled into a spiral shape.

The inside diameter of said spiral is generally between 1 and 20 cm, and preferably between 2 and 6 cm.

The laboratory reactor according to the invention generally comprises a heating jacket completely surrounding said reactor such that the temperature profile within the reactor is isothermal.

The reactor according to the invention can optionally include at its two ends a system of wires blocking any movement of the catalyst grains within the tube or tubes comprising the reactor.

The reactor according to the invention can be used especially to study hydrotreatment and/or hydrogenation reactions of any petroleum fractions.

More generally, the reactor according to the invention makes possible the kinetic study of any catalytic reaction calling for a gaseous phase and a liquid phase.

DETAILED DESCRIPTION OF THE INVENTION

The reactor according to the invention can be described as a tubular reactor whose essentially constant diameter is calculated so as to allow every cross-section to be occupied by a defined number of catalyst grains, this number remaining substantially constant over the entire length of the reactor. Typically, this number of grains in a reactor section can be 1, 2, 3 or 4, but most often it will be 1.

Figure 3:
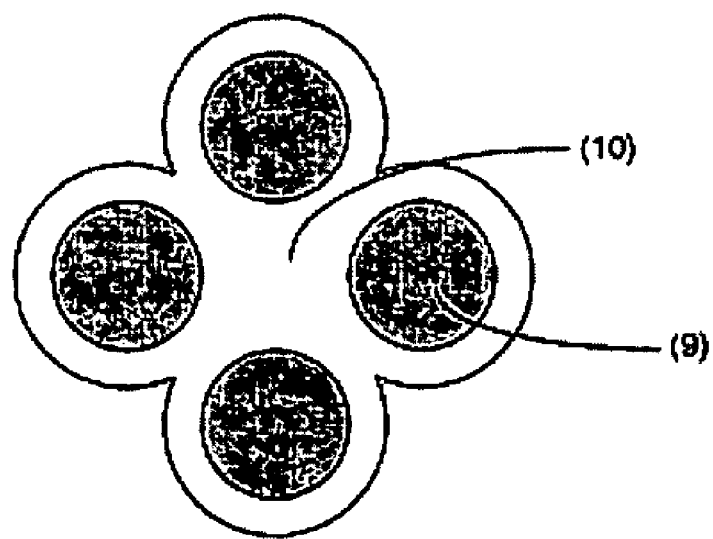
FIG. 3 is a view of a section of the reactor containing 4 grains with an adapted wall shape, called a cloverleaf.

In the case in which the number of grains per cross-section is greater than 1, for example 4, the shape of the wall of the tube can be adapted so as to facilitate the introduction of the grains into the capillary tube, as is illustrated in FIG. 3 that shows by way of example a grain of cylindrical shape (9) occupying a section of the tube (1), said cross-section itself having a cloverleaf shape.

Figure 4:
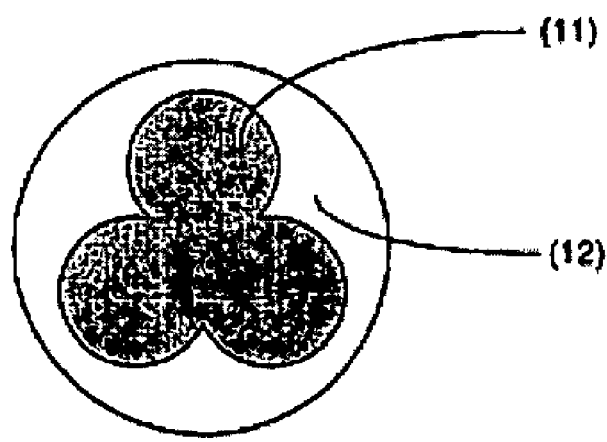
FIG. 4 is a view of a section of the reactor containing a grain with a trefoil shape.

By way of an example that is in no way limiting, FIG. 4 shows a grain of trefoil shape (11) occupying the cylindrical section (12) of a reactor according to the invention.

Any external shape of the wall of the capillary tube that facilitates introduction and positioning of the grains within the tube is suited to this invention.

The shape of the grains is generally spherical or cylindrical and the diameter of the grain must then be understood as being that of the sphere or that of the corresponding cylinder, respectively. The field of the invention includes crushed grains, and more generally grains of any shape.

In practice, in the case in which the section of the reactor is occupied by a single grain of spherical shape or essentially spherical shape, the relationship between the grain diameter (Dg) and the reactor internal diameter (Dr) is such that Dr/Dg is less than 2, and preferably between 1.1 and 2.

In the case of a catalyst grain of nonspherical or noncylindrical shape, the idea of diameter equivalent to the direction of the diameter of a sphere satisfying the ratio (external surface)/(volume) of the grain under consideration will be adopted as the characteristic dimension. In this case, Dr/De is less than 2, and preferably between 1.1 and 2.

The invention extends via the equivalent diameter to catalyst particles of any shape.

Depending on the number of catalyst grains contained in the cross-section of the reactor, the relationship between the equivalent diameter of the grain (De) and the reactor diameter (Dr) is given by Table 1.

TABLE 1

Preferred Range of Dr/De Values Based on the Number of Catalyst Grains Contained in the Reactor Section

| N | Minimum Dr/De | Maximum Dr/De |
| --- | --- | --- |
| 1 | 1.1 | 2.0 |
| 2 | 2.1 | 2.3 |
| 3 | 2.3 | 2.5 |
| 4 | 2.5 | 2.7 |

The reactor length is another dimensioning parameter. It follows from the number of catalyst grains that must be used to achieve the desired volumetric flow rate (VVH).

In general, the mass of the catalyst used in the reactor will be between 0.1 gram and 50 grams, and preferably between 1 and 20 grams.

If the length of the reactor becomes significant, for example roughly 1 meter, for reasons of compactness, it is possible to roll the capillary tube into a spiral shape whose inside diameter will be between 1 and 20 cm, and preferably between 2 and 6 cm.

In no case does the spiral shape limit the shape of the reactor according to the invention, and a capillary reactor of any shape remains quite within the framework of the invention.

The spiral shape or any other shape is intended solely to obtain a sufficiently compact reactor for practical reasons.

One important aspect in the dimensioning of the reactor tube is the consideration of the superficial velocity of the liquid that is defined as the ratio of the liquid flow rate to the empty section of the reactor.

To ensure undisturbed flow, the liquid superficial velocity must be greater than a critical velocity that is fixed at 0.3 mm/s and preferably greater than 0.5 mm/s.

In the capillary reactor according to the invention, the flow mode of the reaction phases can be equally in ascending or descending co-current. In contrast to the laboratory reactors according to the prior art, the ascending or descending nature of the flow of the reaction phases has no effect on the results obtained with the reactor according to the invention.

Figure 2:
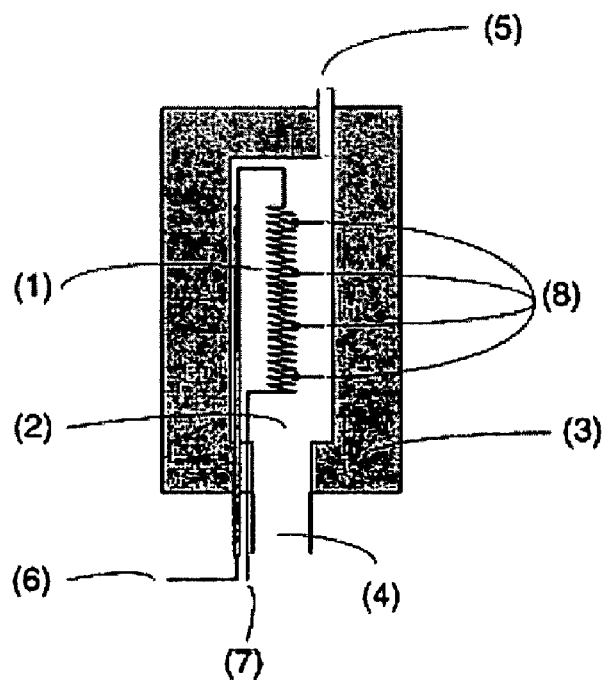
FIG. 2 is a general outline of the reactor according to the invention with its heating jacket.

The invention will be better understood by following FIGS. 1 and 2.

FIG. 1 shows a tubular reactor according to the invention, the tube being rolled in the shape of a spiral. The ends (6) and (7) correspond to the entry of fluids and the exit of reaction fluids in an ascending flow mode. The zones labelled (B); (A); (C) correspond to the inert downstream zone, the reaction zone and the inert upstream zone, respectively.

The terms upstream and downstream are defined relative to the reaction zone following the fluid flow. Let us remember that the direction of fluid flow has no effect on the performance of the reactor according to the invention. The end (7) can thus correspond to the entry of fluids, and the end (6) can correspond to the exit of fluids in a descending flow mode.

Most of the studied reactions have a thermal effect, and it is often necessary to study the reaction with respect to a certain temperature profile along the reactor. The addition or withdrawal of calories is accomplished via a heating or cooling fluid that is generally introduced into a heating (or cooling) jacket surrounding the capillary reactor, as shown in FIG. 2.

The heating fluid enters by the end (4) and exits by the end (5) of the heating jacket (2). The capillary reactor arranged in the form of a spiral (1) is located within the heating jacket (2). The heating jacket is itself insulated from heat exchange with the exterior by a heat insulation system labelled (3) in FIG. 2.

The temperature profile along the capillary reactor is generally tracked by means of thermocouples (8) located at different elevations along the reactor.

The catalyst grains are generally kept blocked in their position by a system of stainless wires that occupy the parts of the reactor located upstream and downstream from the zone that is loaded with the catalyst grains. Due to the spiral shape of the reactor, the wire cannot move, and consequently it can support the catalytic bed and limit all of its movements. Inert grains could likewise be used in place of the wire, and a system of grids could be installed at the input and output of the reactor to keep them in their place.

The capillary reactor according to the invention can be used for kinetic study of the reactions calling for a liquid feedstock and a gaseous co-reagent. It is especially well suited for the study of hydrotreatment and hydrogenation reactions of hydrocarbon fractions that can require pressures of up to 10 MPa or 20 MPa, and temperatures of generally between 150° C. and 500° C.

The pressure level dictates the thickness of the tube used, according to any method that is well known to one skilled in the art.

COMPARISON EXAMPLE

The example selected to illustrate the invention is that of the hydrodesulfurization of a gas oil fraction, composed of hydrocarbons with between 12 and 25 carbon atoms.

The density of this gas oil fraction is 0.854 gram/milliliter (1 milliliter=$10^{-3}$ liter).

The reaction develops at a temperature of 340° C. and a pressure of 5.1 MPa, in the presence of a nickel- and molybdenum-based catalyst that is deposited on a gamma-alumina substrate with a specific surface area of 250 grams/cm².

The sulfur content of the gas oil is 13,500 ppm, and the content desired at the output is 50 ppm. The desired conversion must thus be 99.5%.

The catalyst is present in the form of trefoil-shaped particles with a diameter equivalent to 1.2 mm. The results obtained in a laboratory reactor according to the prior art and in a capillary reactor according to the invention are compared.

1) Laboratory Reactor (According to the Prior Art)

The reactor according to the prior art is defined by the following dimensions:
Inside diameter: 8 mm
Height of catalyst bed: 167 mm
Catalyst mass that is introduced: 5.5 grams
Volumetric flow rate: 1 $h^{-1}$
Gas/liquid ratio: 440 Nl/l (Nl means normal liter, i.e., under standard conditions T=25° C. and P=105 bars)
Liquid superficial velocity: 0.05 mm/s
Gas superficial velocity: 0.6 mm/s The catalytic bed is diluted by introducing fine carborundum ("silicon carbide") particles, chemically inert, with a mean diameter of 250 microns.

2) Capillary Reactor (According to the Invention)

The capillary reactor according to the invention has the following dimensions:
Internal tube diameter: 2.1 mm
Tube length (for the catalytic zone): 5000 mm
Catalyst mass that is introduced: 5.5 grams
Volumetric flow rate: 1 $h^{-1}$
Gas/liquid ratio: 440 Nl/l
Liquid superficial velocity: 0.7 mm/s
Gas superficial velocity: 9 mm/s The capillary tube is rolled into the shape of a spiral with an inside diameter of 30 mm.

The tube used is a stainless steel tube of reference SS316.

The catalytic zone is preceded by an inert zone containing a stainless wire for holding the catalyst grains to allow stabilization of the flow before reaching the catalytic zone.

This inert zone has a length of: 1.5 m.

The temperature profile is maintained along the reactor by a heating system comprising a heating jacket surrounding the reactor and supplied with hot air.

The overall dimensions of the reactor and its heating system are 500 mm of height and 310 mm of diameter.

Table 2 below summarizes the performances of the reactor according to the prior art and the reactor according to the invention, expressed by the residual amount of sulfur measured at the output for different values of the VVH.

The reactor performance or conversion is proportionately better the lower the residual sulfur at the output.

For the reactor according to the prior art, an ascending flow mode and a descending flow mode are distinguished. This distinction was not made for the reactor according to the invention.

TABLE 2

| | Reactor and Type of Bed | | |
|---|---|---|---|
| VVH ($h^{-1}$) | Tubular Prior Art 250 μm of SiC Descending | Tubular Prior Art 250 μm of SiC Ascending | Capillary (According to the Invention) Descending or Ascending |
| | Residual Sulfur Content (ppm) | | |
| 2.0 | 353 | 398 | 258 |
| 1.0 | 30 | 51 | 12 |
| 0.5 | 9 | 5 | 2 |

Another important point that must be noted is the insensitivity of the performances of the capillary reactor to the direction of fluid flow, whereas the ascending or descending flow direction influences the performances of the reactor according to the prior art.

The conversion level obtained with the capillary reactor did not vary over time within a period of 70 hours, whereas it dropped 30% over the same period for the reactor according to the prior art.

The capillary reactor according to the invention thus makes it possible to obtain stable conversion levels, a necessary precondition for kinetic studies. Moreover, the conversion levels obtained are clearly higher than those obtained with reactors according to the prior art (residual sulfur content clearly less), which is an indicator of an elimination of mass transfer limitations. The reactor according to the invention thus makes it possible to study the intrinsic kinetics of the catalyst.

By the term "every cross-section" of the reactor is meant on average every cross-sectional location perpendicular to the axis of the tube. Thus, "every cross-section" implicitly includes sufficient length of the tube to form a unit which will accommodate the lengthwise dimension of a catalyst particle. Accordingly, "every cross-section" is defined in the following claims as every cross-sectional unit.

The entire disclosures of all applications, patents and publications, cited herein and of corresponding French Application No. 05/03.921 filed Apr. 18, 2005 are incorporated by reference herein.

Without further elaboration, it is believed that one skilled in the art can, using the preceding description, utilize the present invention to its fullest extent. The foregoing preferred specific embodiments are, therefore, to be construed as merely illustrative, and not limitative of the remainder of the disclosure in any way whatsoever.

In the foregoing, all temperatures are set forth uncorrected in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A laboratory reactor for the kinetic study of catalytic reactions calling for a gaseous reaction phase and a liquid reaction phase, said reactor comprising: a tubular reactor having a capillary shape with an internal diameter (Dr), a fixed bed of catalyst grains wherein said fixed bed is in the form of a uniform arrangement of the catalyst grains within the reactor, every cross-sectional unit of the reactor comprising a defined and constant number of catalyst grains, and said number of catalyst grains being 1, 2, 3, or 4, said grains having a diameter (Dg) of that of an essentially spherical shape or an essentially cylindrical shape, or an equivalent diameter (De) of a shape having a surface to volume ratio of essentially that of a sphere and wherein the ratio of Dr to De is dependent on the grain number per cross sectional unit and wherein:
   where the grain number is 1, the ratio of Dr to De is between 1.1 and 2,
   where the grain number is 2, the ratio of Dr to De is between 2.1 and 2.3,
   where the grain number is 3, the ratio of Dr to De is between 2.3 and 2.5,
   where the grain number is 4, the ratio of Dr to De is between 2.5 and 2.7.

2. A laboratory reactor according to claim 1, in which the grain number is 1 and, the ratio between the internal diameter of the reactor (Dr) and the equivalent diameter of the grain (De) is between 1.1 and 2.

3. A laboratory reactor according to claim 1, in which the catalyst grain number per cross-sectional unit is 2, and the ratio between the internal diameter of the reactor (Dr) and the equivalent diameter of the grain (De) is between 2.1 and 2.3.

4. A laboratory reactor according to claim 1, in which the catalyst grain number per cross-sectional unit is 3, and the ratio between the internal diameter of the reactor Dr) and the equivalent diameter of the grain De is between 2.3 and 2.5.

5. A laboratory reactor according to claim 1, in which the catalyst grain number per cross-sectional unit is 4, and the ratio between the diameter of the reactor (Dr) and the equivalent diameter of the grain (De) is between 2.5 and 2.7.

6. A laboratory reactor according to claim 1, in which the reactor contains a total catalyst mass between 0.1 and 50 grams.

7. A laboratory reactor according to claim 1, in which the tube or tubes comprising a reactor module are rolled into a spiral shape, the inside diameter of said spiral being between 1 and 20 cm.

8. A laboratory reactor according to claim 1, comprising a heating jacket completely surrounding said reactor with adjustable controls such that an isothermal temperature profile within the reactor can be maintained.

9. A laboratory reactor according to claim 1, in which the reactor includes at its two ends a system of wires blocking any movement of the catalyst grains.

10. A laboratory reactor according to claim 6, in which the reactor contains a total catalyst mass between 1 and 10 grams.

11. A laboratory reactor according to claim 8, in which the tube or tubes comprising a reactor module are rolled into a spiral shape, the inside diameter of said spiral being between 2 and 6 cm.

12. A laboratory reactor according to claim 3, in which the tube or tubes comprising a reactor module are rolled into a spiral shape, the inside diameter of said spiral being between 1 and 20 cm.

13. A laboratory reactor according to claim 4, in which the tube or tubes comprising a reactor module are rolled into a spiral shape, the inside diameter of said spiral being between 1 and 20 cm.

14. A laboratory reactor according to claim 5, in which the tube or tubes comprising a reactor module are rolled into a spiral shape, the inside diameter of said spiral being between 1 and 20 cm.

15. In a process of analyzing hydrotreatment and hydrogenation reactions of a petroleum fraction comprising providing a laboratory unit according to claim 1 and conducting a hydrotreatment and/or hydrogenation reaction within said laboratory unit, comprising passing a liquid phase petroleum fraction into said laboratory unit.

16. A process according to claim 15 wherein said liquid phase exhibits a superficial velocity greater than 0.3 mm/sec.

17. A process according to claim 15 wherein said liquid phase exhibits a superficial velocity greater than 0.5 mm/sec.

18. A laboratory reactor according to claim 1, wherein said tubular reactor has a cloverleaf cross-section.

19. A laboratory reactor according to claim 1, wherein said tubular reactor has a trefoil cross-section.

20. A laboratory reactor according to claim 1, wherein the length of the tubular reactor is at least 100 times longer than the diameter of the reactor.

21. A laboratory reactor according to claim 7, wherein the length of the tubular reactor is at least 100 times longer than the diameter of the reactor.

* * * * *

UNITED STATES PATENT AND TRADEMARK OFFICE
CERTIFICATE OF CORRECTION

PATENT NO.      : 7,588,734 B2                                    Page 1 of 1
APPLICATION NO. : 11/405677
DATED           : September 15, 2009
INVENTOR(S)     : Bellos et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 234 days.

Signed and Sealed this

Twenty-first Day of September, 2010

David J. Kappos
*Director of the United States Patent and Trademark Office*